US011249187B2

(12) United States Patent
Ing et al.

(10) Patent No.: US 11,249,187 B2
(45) Date of Patent: Feb. 15, 2022

(54) METHOD AND ACOUSTIC DEVICE FOR MEASURING SURFACE MOVEMENTS (71) Applicants: CENTRE NATIONAL DE LA RECHERCHE SCIENTIFIQUE (CNRS), Paris (FR); ECOLE SUPÉRIEURE DE PHYSIQUE ET DE CHIMIE INDUSTRIELLES DE LA VILLE DE PARIS, Paris (FR); SORBONNE UNIVERSITE, Paris (FR); INSERM (INSTITUT NATIONAL DE LA SANTÉ ET DE LA RECHERCHE MEDICALE), Paris (FR); UNIVERSITÉ PARIS DIDEROT—PARIS 7, Paris (FR)

(72) Inventors: Ros Kiri Ing, Ivry-sur-Seine (FR); Nathan Jeger-Madiot, Paris (FR); Mathias Fink, Meudon (FR); Thomas Similowski, Issy les Moulineaux (FR)

(73) Assignees: CENTRE NATIONAL DE LA RECHERCHE SCIEN TIFIQUE (CNRS), Paris (FR); ECOLE SUPÉRIEURE DE PHYSIQUE ET DE CHIMIE INDUSTRIELLES DE LA VILLE DE PARIS, Paris (FR); SORBONNE UNIVERSITE, Paris (FR); INSERM (INSTITUT NATIONAL DE LA SANTÉ ET DE LA RECHERCHE MEDICALE), Paris (FR); UNIVERSITÉ PARIS DIDEROT—PARIS 7, Paris (FR)

( * ) Notice: Subject to any disclaimer, the term of this patent is extended or adjusted under 35 U.S.C. 154(b) by 600 days.

(21) Appl. No.: 16/319,445

(22) PCT Filed: Jul. 10, 2017

(86) PCT No.: PCT/FR2017/051883
§ 371 (c)(1),
(2) Date: Jan. 21, 2019

(87) PCT Pub. No.: WO2018/015638
PCT Pub. Date: Jan. 25, 2018

(65) Prior Publication Data
US 2019/0331793 A1    Oct. 31, 2019

(30) Foreign Application Priority Data

Jul. 21, 2016    (FR) .................................... 1656935

(51) Int. Cl.
*G01S 15/00*    (2020.01)
*G01S 15/50*    (2006.01)
(Continued)

(52) U.S. Cl.
CPC .............. *G01S 15/50* (2013.01); *G01S 15/36* (2013.01); *A61B 5/11* (2013.01); *A61B 8/15* (2013.01); *A61B 8/4477* (2013.01)

(58) Field of Classification Search
USPC ........................................................ 367/99
See application file for complete search history.

(56) References Cited

U.S. PATENT DOCUMENTS 4,122,427 A    10/1978    Karsh
4,197,856 A    4/1980    Northrop
(Continued)

OTHER PUBLICATIONS

International Search Report issued in PCT/FR2017/051883 dated Oct. 19, 2017 (7 pages).
(Continued)

*Primary Examiner* — James R Hulka
(74) *Attorney, Agent, or Firm* — Osha Bergman Watanabe & Burton LLP (57) ABSTRACT

A method for detecting movements of a plurality of points (P) of a surface (21), comprising a measuring step during
(Continued)

which an incident ultrasonic wave is emitted into the air towards the surface and an ultrasonic wave reflected into the air by the surface (21) is detected. During the measuring step, each measuring point is illuminated by the incident ultrasonic wave at a multiplicity of angles of incidence, and the reflected ultrasonic wave is detected by a network of receiving transducers (3) comprising a plurality of ultrasonic receiving transducers (3a). The movements of the surface are determined at a measuring point by determining a delay and/or a phase shift between two beam-forming signals for said measuring point.

22 Claims, 5 Drawing Sheets (51) Int. Cl.
*G01S 15/36* (2006.01)
*A61B 5/11* (2006.01)
*A61B 8/15* (2006.01)
*A61B 8/00* (2006.01)

(56) References Cited

U.S. PATENT DOCUMENTS

| 8,590,381 | B2* | 11/2013 | Murai | G01N 29/043 |
| | | | | 73/602 |
| 9,081,113 | B2* | 7/2015 | Poggiagliolmi | G01H 9/008 |
| 2009/0178483 | A1* | 7/2009 | Angelsen | G01S 7/52095 |
| | | | | 73/597 |
| 2010/0036244 | A1* | 2/2010 | Angelsen | G01S 15/8952 |
| | | | | 600/438 |
| 2011/0030479 | A1* | 2/2011 | Murai | G01N 29/28 |
| | | | | 73/632 |
| 2011/0208060 | A1 | 8/2011 | Haase et al. | |
| 2013/0079640 | A1* | 3/2013 | Osawa | A61B 8/4477 |
| | | | | 600/447 |
| 2014/0150556 | A1* | 6/2014 | Angelsen | G01S 7/52077 |
| | | | | 73/627 |
| 2015/0018688 | A1* | 1/2015 | Osawa | G01S 7/52077 |
| | | | | 600/459 |
| 2015/0078131 | A1 | 3/2015 | Poggiagliolmi | |
| 2015/0289837 | A1* | 10/2015 | Kim | A61B 8/5223 |
| | | | | 600/454 |
| 2017/0143295 | A1* | 5/2017 | Park | A61B 8/5253 |
| 2019/0046162 | A1* | 2/2019 | Tsushima | A61B 8/4272 |

OTHER PUBLICATIONS

Written Opinion of the International Searching Authority issued in PCT/FR2017/051883 dated Oct. 19, 2017 (5 pages).

Catheline, S. et al.; "Acoustic source localization model using in-skull reverberation and time reversal"; Applied Physics Letters, A I P Publishing LLC, US, vol. 90, No. 6, Feb. 7, 2007 (3 pages).

Etaix, N. et al.; "Acoustic imaging device with one transducer"; The Journal of the Acoustical Society of America, American Institute of Physics for the Acoustical Society of America, New York, NY, US, vol. 131, No. 5, May 1, 2012, (5 pages).

Etaix, N. et al.; "Increasing the modal density in plates for monoelement focusing in air"; The Journal of the Acoustical Society of America, vol. 134, No. 2, Aug. 1, 2013, ( 7 pages).

Quieffin, N. et al.; "2D pseudo-array using an ultrasonic one channel time-reversal mirror"; 2004 IEEE Ultrasonics Symposium, vol. 1, Aug. 23, 2004, pp. 801-804 (4 pages).

* cited by examiner

METHOD AND ACOUSTIC DEVICE FOR MEASURING SURFACE MOVEMENTS

TECHNICAL FIELD OF THE INVENTION

The present invention relates to methods and acoustic devices for detecting surface movements.

More particularly, the invention relates to a method for detecting movements of a surface, comprising a measuring step during which at least one incident ultrasonic wave is emitted into the air towards the surface using an ultrasonic wave emitting device and reflected signals representative of at least one ultrasonic wave reflected in the air by said surface from said at least one incident ultrasonic wave are detected.

Document U.S. Pat. No. 4,122,427 describes an example of such a method, in which the movements of a surface on a measuring channel are measured, by emitting ultrasound at a frequency of the order of 40 Hz towards the surface. Ultrasound is emitted by a single transducer.

SUMMARY OF THE INVENTION

The purpose of the present invention is in particular to further improve this type of method, in particular to enable a better detection efficiency of surface movements.

For this purpose, according to the invention, a method of the type in question is characterized in that, during each measurement:

the movements of a plurality of measuring points belonging at least to said surface are measured by illuminating each measuring point with said at least one incident ultrasonic wave at a multiplicity of angles of incidence, the reflected signals are detected using a network of receiving transducers comprising a plurality of ultrasonic receiving transducers and a beam-forming signal is determined for each measuring point by at least beam-forming in reception from said reflected signals, and in that it further comprises at least one movement determination step during which said movements of the surface at the considered measuring point are determined by determining at least one delay or phase shift between two beam-forming signals for this measuring point.

Thanks to these provisions, the movements of a wide variety of liquid or solid, whether smooth or rough, flat or not, surfaces can be measured, regardless of their transparency to light. Surface movements can be imaged over a large area, for example several tens of cm$^2$, at a rate of up to one kilohertz or more. The sensitivity of the measuring method of the invention reaches one micrometer for a minimum detectable speed of the order of one fraction of a millimetre per second. Eventually, the acoustic power used can be low, for example with a level of the order of 60-70 dB SPL (sound pressure level).

In preferred embodiments of the method according to the invention, one and/or the other of the following provisions may also be used:

during each measuring step, each measuring point of the surface is illuminated with said at least one incident wave at angles of incidence extending over a range of angles of incidence of at least 20 degrees;

during each measuring step, the movements are measured at substantially any point of the surface over an area greater than 10 cm$^2$;

the ultrasonic wave emitting device and the network of receiving transducers are two-dimensional;

the network of emitting transducers (2) has an aperture at least equal to an aperture of the ultrasonic wave receiving device in two substantially perpendicular directions;

the aperture of the network of emitting transducers is equal to at least three times the aperture of the ultrasonic wave receiving device, in at least one of the directions;

the aperture of the ultrasonic wave emitting device is at least equal to 20 cm in each direction;

the ultrasonic wave emitting device comprises a network of emitting transducers comprising a plurality of ultrasonic emitting transducers;

the ultrasonic emitting transducers are divided into several groups and, during said measuring step, a same signal is simultaneously emitted by the ultrasonic emitting transducers belonging to a same group;

the ultrasonic wave emitting device comprises at least one ultrasonic emitting transducer so arranged as to emit into a mixing cavity adapted to cause multiple reflections of said at least one incident ultrasonic wave before sending it to the surface;

the ultrasonic waves have a frequency of less than 100 kHz;

the ultrasonic waves are emitted at a rate above 500 shots per second;

during each step of measuring index k, a beam-forming signal $S_k$ in reception is calculated at said point, at least at different points of the surface, and during each movement determination step, the movement of each point of the surface is determined by determining a delay or phase shift between the beam-forming signal $S_k$ in reception at said point, for two different k values.

during each step of measuring index k, the ultrasonic wave emitting device emits a non focused incident ultrasonic wave towards the surface;

during each step of measuring index k, the ultrasonic wave emitting device successively emits focused incident ultrasonic waves towards the different points of the surface and the beam-forming signal $S_k$ in reception at said point is determined from the reflected signals corresponding to the focused incident ultrasonic wave at said point;

the beam-forming signal $S_k$ in reception is determined by the following formula:

$$S_k(t) = \sum_{j=1}^{N} r_j\left(t - \frac{d_j}{C}\right)$$

where:

$r_j$ is the signal detected by the ultrasonic receiving transducer (3a) of index j, t is time, $d_j$ is a distance between the point P and the ultrasonic receiving transducer (3a) of index j, c is the speed of the ultrasonic wave in the air.

the ultrasonic wave emitting device comprises a network of emitting transducers comprising a plurality of ultrasonic emitting transducers, during each k-index measuring step, respective impulse responses are measured between each ultrasonic emitting transducer and each ultrasonic receiving transducer, and then at least at different points of the surface a beam-forming signal S'k in emission and in reception is calculated at said point, and during each movement determination step, a movement of each point of the surface is determined by determining a delay or phase shift between the beam-forming signals S'k in emission and in reception at said point, for two different k values;

each beam-forming signal in emission and in reception at said point is determined by the following formula:

$$S'_k(t) = \sum_{j=1}^{N} \sum_{i=1}^{M} h_{i,j,k}\left(t - \frac{d_{ij}}{c}\right),$$

where:
i is an index between 1 and M referring to an ultrasonic emitting transducer,
j is an index between 1 and N referring to an ultrasonic receiving transducer,
$h_{ijk}$ is the impulse response between the ultrasonic emitting transducer of index i and the ultrasonic receiving transducer of index j,
t is time,
$d_{ij}$ is a distance travelled by an ultrasonic wave from the ultrasonic emitting transducer of index i to the ultrasonic receiving transducer of index j by reflecting at the considered point (P) of the surface,
c is the speed of the ultrasonic waves in the air;
during at least some measuring steps, a beam-forming signal is determined for each measuring point of a predetermined observation area and the measuring points belonging to the surface are determined as those which maximize the beam-forming signal;
during the movement determination step, a delay dt between beam-forming signals corresponding to two measuring steps at the same measuring point is determined and:
a travel δ at the measuring point as being proportional to dt·c
and/or a speed at the measuring point as being proportional to dt·c/Δt,
where c is the speed of the ultrasonic waves in the air and Δt is a time interval between said two measuring steps;
during the movement determination step, a phase shift φ is determined between beam-forming signals corresponding to two measuring steps at the same measuring point, as well as:
a travel δ at the measuring point as being proportional to c·φ/(2·π·f)
and/or a speed at the measuring point as being proportional to c·φ/(2·π·f)/Δt,
where c is the speed of the ultrasonic waves in the air, f is the frequency of the ultrasonic waves and Δt is a time interval between said two measuring steps.

In addition, the invention also relates to a device for detecting movements of a surface reflecting ultrasonic waves, comprising an ultrasonic wave emitting device, an ultrasonic wave receiving device, a control device controlling the ultrasonic wave emitting device and receiving signals received by the ultrasonic wave receiving device, with the control device being adapted to perform several successive measuring steps during each of which the ultrasonic wave emitting device emits at least one incident ultrasonic wave into the air towards the surface and the ultrasonic wave receiving device receives reflected signals representative of at least one ultrasonic wave reflected into the air by said surface from said at least one incident ultrasonic wave, characterized in that the ultrasonic wave emitting device is adapted to illuminate a plurality of measuring points (P) belonging at least to said surface (21) by said at least one incident ultrasonic wave at a multiplicity of angles of incidence, in that the ultrasonic wave receiving device is a network of receiving transducers comprising a plurality of ultrasonic receiving transducers, in that the control device is adapted to determine, during each measuring step, a beam-forming signal for each measuring point, by beam-forming at least in reception from said reflected signals, and in that the control device is adapted to determine said surface movements at the considered measuring point by determining at least one delay or phase shift between two beam-forming signals for that measuring point.

Other characteristics and advantages of the invention will appear during the following description of one of its embodiments, given as an example without limitation, while referring to the attached drawings.

In the drawings.

In the different figures, the same references refer to identical or similar elements.

Figure 1:
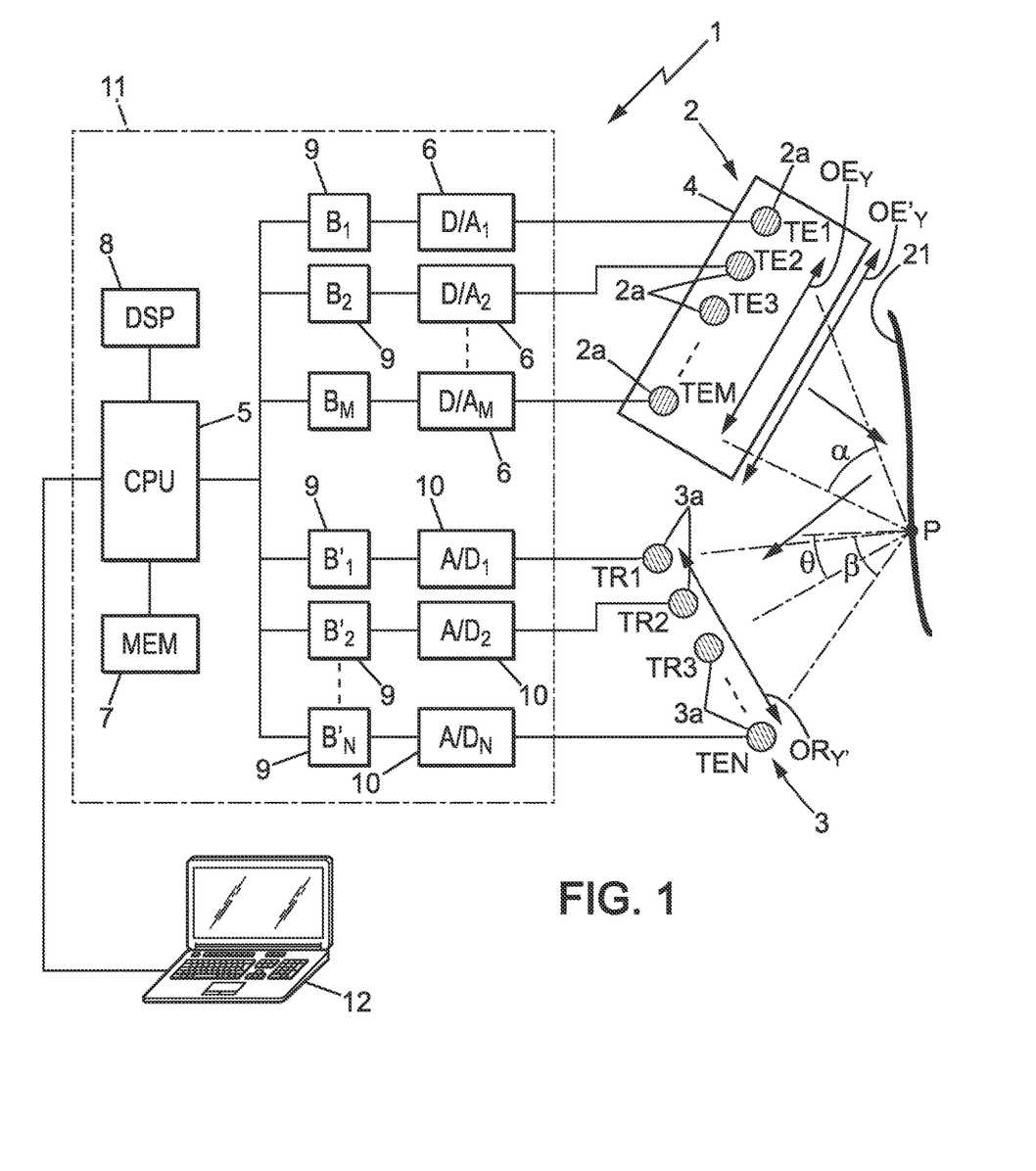
FIG. 1 is a schematic overview of an example of an ultrasonic wave generating device implementing the invention.

FIG. 1 shows an ultrasonic device 1 for measuring the movements of a surface 21, which can be of any kind, whether solid or liquid. The surface 21 can be, for example, the skin of a human being or of an animal.

The ultrasonic device 1 comprises a network of emitting transducers 2, which may include one or more M ultrasonic emitting transducer(s) 2a (TE1, TE2, . . . TEM), and a network of receiving transducers 3, which includes several ultrasonic receiving transducers 3a (TR1, TR2, . . . TRN) in a number of N.

Both networks of transducers 2, 3 can advantageously be two-dimensional networks.

Both networks 2, 3 can possibly be arranged on a same support and, in this case, the transducers 2a, 3a can be interposed between each other.

The transducers 2a, 3a can be of any known type. In one embodiment, the ultrasonic emitting transducers 2a can be high bandwidth loudspeakers and the ultrasonic receiving transducers 3a can be high bandwidth microphones.

The ultrasonic emitting transducer(s) 2a may optionally be arranged to emit ultrasonic waves into a mixing cavity 4 before being sent to the surface 21, as will be described below.

The network of emitting transducers 2 and the network of receiving transducers 3 are intended to measure the movements of a plurality of measuring points P belonging to the surface 21, for example to measure the movements at substantially any point of the surface 21 over an area greater than 10 cm2 and possibly several tens of cm$^2$.

For this purpose, the network of emitting transducers 2 and the network of receiving transducers 3 are each designed to have a relatively large aperture, so that each measuring point P of the surface 21 is illuminated at a large number of angles of incidence by incident ultrasonic waves from the network of emitting transducers 2, and so that each point P of the surface 21 is seen by the receiving transducers 3a at a large number of angles of view.

Figure 2:
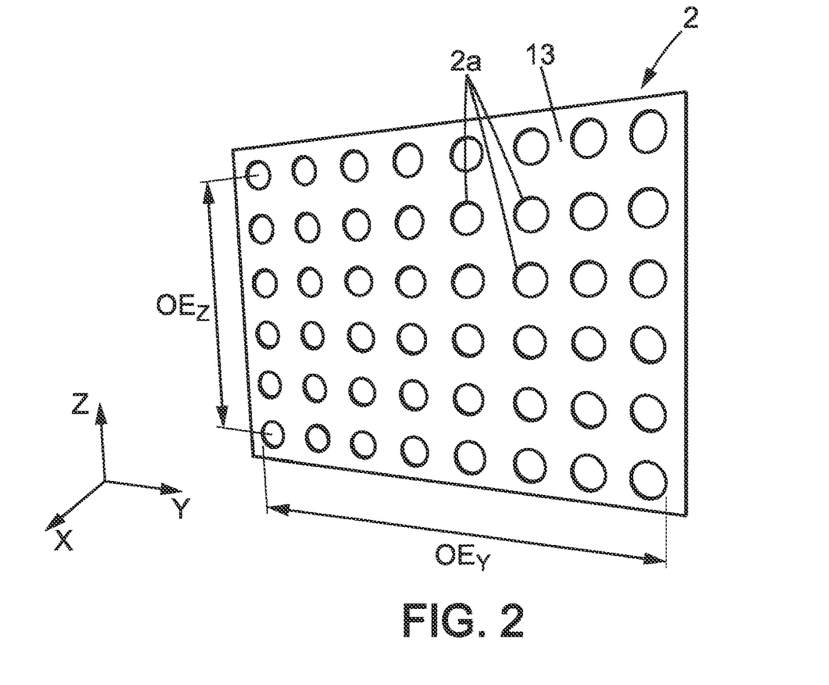
FIG. 2 shows an example of a network of emitting transducers that can be used in the present invention.
Figure 5:
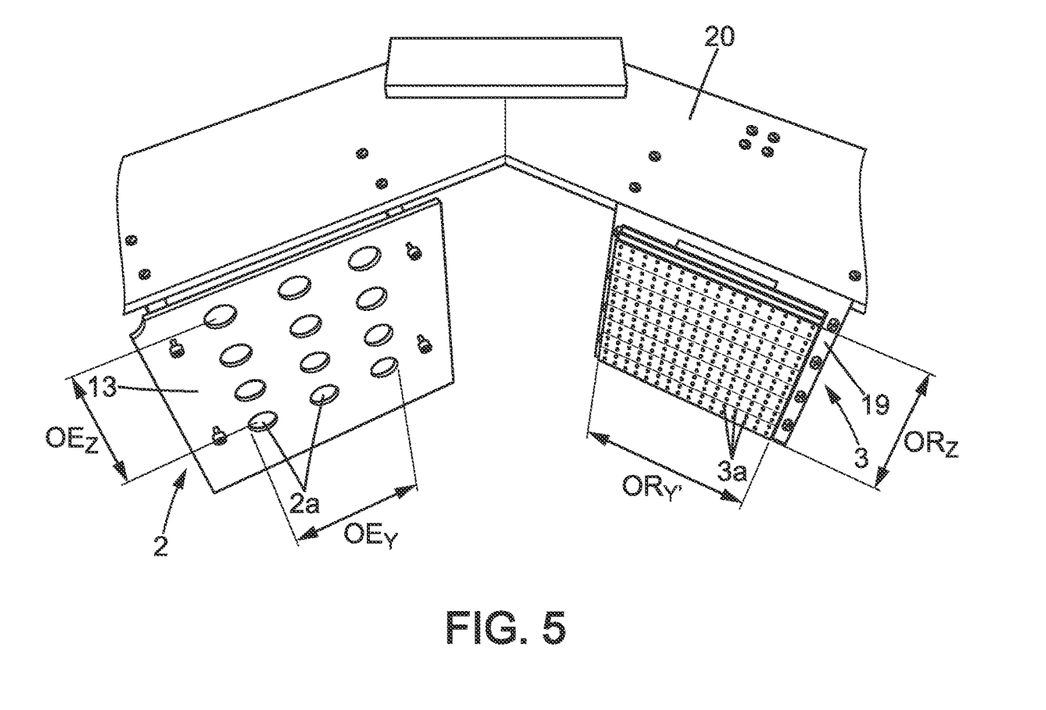
FIG. 5 is a perspective schematic view showing the network of emitting transducers and the network of receiving transducers assembled on a support.

The aperture of the emitting transducer network 2 can be defined as the transverse dimensions $OE_Y$, $OE_Z$ of the network, for example along a vertical Z axis and a transverse horizontal Y axis (see FIGS. 1, 2, 5). This aperture corresponds to an aperture angle α in emission at which the network of emitting transducers 2 is seen from each measuring point P. Each measuring point P is thus illuminated by incident ultrasonic waves at a multiplicity of angles of incidence forming a range of angles of incidence of width α. The aperture angle α can be at least equal to 20 degrees, for example.

The aperture of the network of receiving transducers 3 can be defined as the $OR_{Y'}$, $OR_Z$ transverse dimensions of the network, for example along a vertical axis Z and a horizontal transverse axis Y' (see FIGS. 1, 5). This aperture corresponds to an aperture angle in reception β under which the network of receiving transducers 3 is seen from each measuring point P. Each measuring point P is thus seen by the ultrasonic receiving transducers 3a under a multiplicity of angles of view forming a range of angles of view with a width β. The aperture angle in reception β can be at least equal to 20 degrees, for example.

The aperture angle in emission a can advantageously be greater than the aperture angle in reception β.

In particular, the aperture of the network of emitting transducers 2 along at least one axis Y, Z, or both axes, is advantageously larger than the aperture of the network of receiving transducers along the corresponding axes Y', Z. This ensures that at least part of the reflected ultrasonic waves always return to the network of receiving transducers 3.

Optionally, the aperture of the network of emitting transducers 2 along at least one axis Y, or Z, or both axes, may be more than 3 times (or even 5 times, or even 7 times) the aperture of the network of receiving transducers along the corresponding axes Y', Z.

The ultrasonic device 1 can be controlled by an electronic circuit 11 which may, in turn, be connected to a computer 12 or similar.

The electronic circuit 11 may include:
- a digital-to-analog converter 6 (D/A1-D/AM) connected to each emitting transducer 2a (E1-EM) and associated, if necessary, with a buffer memory 9 (B1-BN),
- an electronic central unit 5 (CPU) controlled by the computer 12 and controlling each analog-to-digital converter 6,
- at least one central memory 7 (MEM) connected to the electronic central unit 5,
- possibly, a specific signal processing circuit 8 (DSP)
- an analog-to-digital converter 10 (A/D1-A/DN) connected to each receiving transducer 3a (TR1-TRN), and associated respectively with a buffer memory 9 (B'1-B'N).

The ultrasonic emitting transducers 2a can be controlled to emit incident ultrasonic waves at a frequency below 100 kHz, for example between 40 and 70 kHz.

Advantageously, the electronic central unit 5 is adapted to emit the incident ultrasonic waves at a rate greater than 500 shots per second, so that it can follow the movements of the surface 21 over time.

As shown in FIG. 2 in a particular exemplary embodiment, the network of emitting transducers 2 can be a two-dimensional network of ultrasonic emitting transducers 2a carried by a rigid plate 13.

These ultrasonic emitting transducers 2a can be controlled to emit the incident ultrasonic waves either at the same time or sequentially.

If appropriate, the ultrasonic emitting transducers 2a can be divided into several groups and all the ultrasonic emitting transducers 2a of a same group are controlled to simultaneously emit the same signal. This results in a multiplied network, which artificially increases the emitting aperture of the network of emitting transducers 2.

Alternatively or in addition, the network of emitting transducers 2 can be coupled to a mixing cavity 4, as explained above and as shown in FIGS. 1 and 3. The network of emitting transducers 2 can possibly be reduced in this case to a single ultrasonic emitting transducer 2a, since the aperture $OE'_Y$, $OE'_Z$ of the network of emitting transducers 2 is then defined not by the spatial distribution of the transducers but by the dimensions of the emitting face of the mixing cavity, by which the incident ultrasonic waves exit into the air towards the surface 21.

Figure 3:
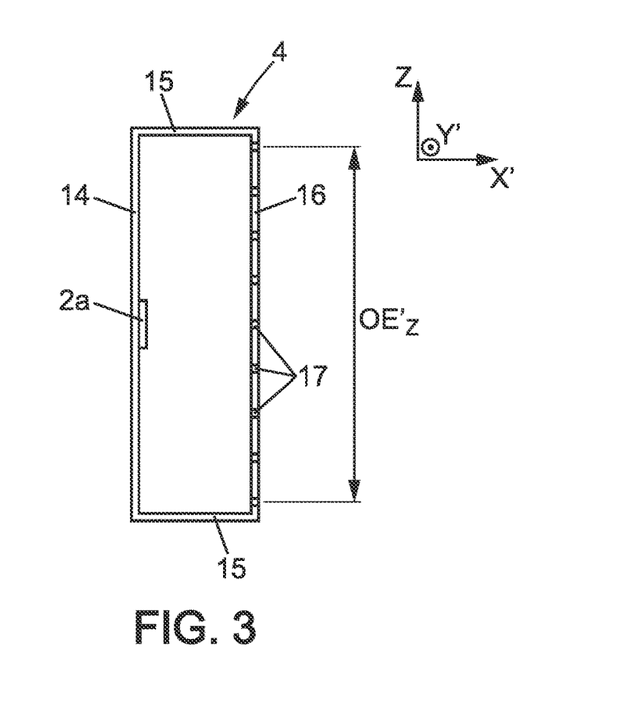
FIG. 3 is a schematic cross-sectional view illustrating an example of a mixing cavity for one or more ultrasonic transducer(s)

The mixing cavity 4 can be a solid object such as a plate or any other one, or it can be a housing in which the network of emitting transducers 2 is mounted, as shown in FIG. 3. In this case, the mixing cavity 4 may have a bottom 14, side walls 15 and an emitting wall parallel to the bottom 14 and be kept away from the bottom 14 by the side walls 15. The network of emitting transducers 2 can be mounted on the bottom 14, in the mixing cavity 4. The emitting wall 16 can have holes 17 enabling the output of the incident ultrasonic waves towards the surface 21. These holes 17 constitute as many ultrasound sources which define the aperture of the network of emitting transducers 2.

Figure 4:
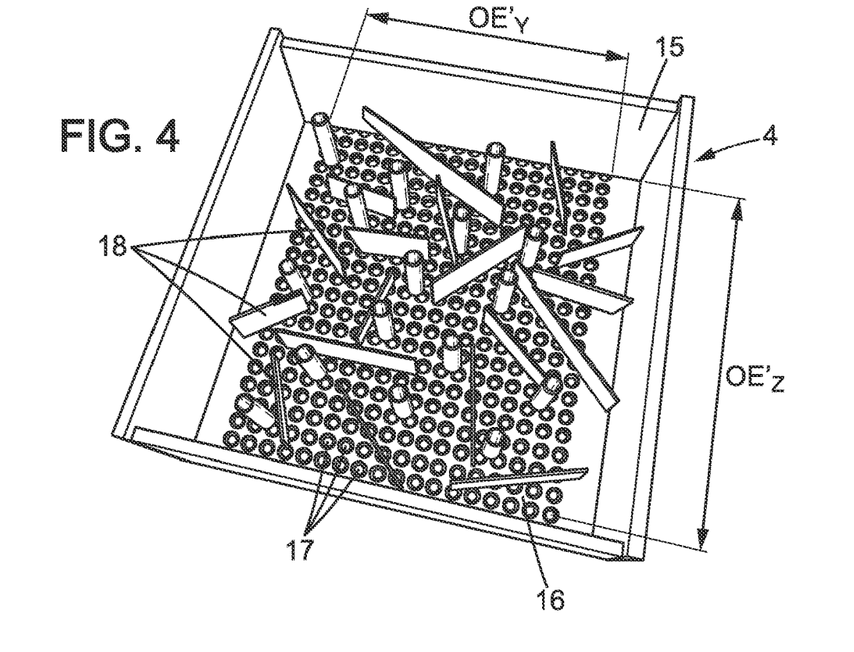
FIG. 4 is a perspective view of the inner portion of the mixing cavity of FIG. 3.

As shown in FIG. 4, reflective walls 18 can be provided inside the mixing cavity, for example attached to the emitting wall 16 and advantageously substantially perpendicular to the bottom 14. The reflective walls 18 are oriented in various ways to promote multiple reflections of the ultrasonic waves in the mixing cavity 4.

The device described above is used to measure the movements of the surface 21, including travel and speed at any point.

This measurement is performed by processing the reflected signals received by the ultrasonic receiving transducers 3a, by a signal processing method which can for example be one of the three methods described below.

Method 1

In this first signal processing method, the illumination of the surface 21 by the incident ultrasonic waves (the incident ultrasonic waves shot) is achieved by simultaneously exciting the M ultrasonic emitting transducers 2a.

At each measuring step k, corresponding to an incident wave shot, the signals received by the ultrasonic receiving transducers 3a are conventionally processed by beam-forming in reception.

Thus, for each point P of the observation area (i.e. the area likely to be occupied by the surface 21), a beam-forming signal $s_k(t)$ in reception is calculated as follows:

$$S_k(t) = \sum_{j=1}^{N} r_j\left(t - \frac{d_j}{c}\right) \qquad (1)$$

Where:

$r_j$ is the signal received by the transducer Rj of the receiving network 3, t is time, $d_j$ is the distance between the point P and the transducer Rj, c is the speed of the ultrasonic wave in the air.

This signal is maximum for the points P belonging to the reflective surface 21.

A topography of the surface 21, and therefore an image of the surface 21, which is however most often approximate can thus be determined.

On the other hand, it is possible to determine very precisely the travels δ at each point P of the surface between two shots k and k+1, by comparing the signals $S_k(t)$ corresponding to the different successive shots.

For a given point P of the surface 21, the successive signals $S_k(t)$ and $S_{k+1}(t)$ are compared during at least one movement determination step, which shows a phase shift φ which is related to the travel δ covered by the point P between the shots k and k+1 perpendicularly to the surface 21, by the relation:

$$\frac{\varphi}{2\pi f} = \frac{2\delta \cos\theta}{c}, \qquad (1)$$

where:

c is the speed of the ultrasonic wave in the air, f is the frequency of the ultrasonic wave θ is the average angle of incidence and of reflection of the ultrasonic wave at point P, i.e. the average angle between the normal to the surface and the reflected beam (as determined according to the topography of the surface 21).

Considering that the surface 21 is reflective for the ultrasonic waves, the travel d of the surface 21 is seen as a travel 2d·cos θ of a virtual source located behind the surface 21, hence the above formula (1).

The travel δ of the point P between the shots k and k+1 is therefore calculated by the formula:

$$\delta = \frac{c \cdot \varphi}{4\pi f \cos\theta}. \qquad (2)$$

In a similar way, not the phase shift φ, but the delay dt=φ/(2πf) of the signal $S_{k+1}(t)$ can be measured relative to $S_k(t)$ (t is counted each time from the incident wave shot), the calculation of the travel δ between the shots k and k+1 being then performed by the formula:

$$\delta = \frac{c \cdot dt}{2 \cdot \cos\theta}. \qquad (2')$$

In both cases, tracking back to the normal speed of the surface 21 can easily be performed: V=δ/Δt, where Δt is the time interval between the shots k and k+1.

This first method is very fast and particularly effective, especially if the surface 21 is illuminated under a wide angular range and therefore if the network of emitting transducers 2 has a wide emission aperture.

Using a multiplied network or a mixing cavity is therefore particularly desirable in this case for the network of emitting transducers 2.

Method 2

In this second signal processing method, a mixing cavity is not preferred for the network of emitting transducers 2.

A pulse wave is successively emitted by each ultrasonic emitting transducer 2a, which is considered as punctual and emitting a spherical wave. Each series of successive shots by all the ultrasonic emitting transducers 2a constitutes a measuring step k, then the shots are repeated in a subsequent series k+1 of successive shots by all the ultrasonic emitting transducers 2a.

For each series k of shots, the impulse response $h_{ijk}(t)$ between each ultrasonic emitting transducer Ei and each ultrasonic receiving transducer TRj is determined.

For a given point P of the area to be observed, the distance to be covered by the ultrasonic wave from the emitter Ei to the receiver Rj, noted $d_{ij}$ is known. This distance is known for all pairs (Ei,Rj).

A beam-forming signal in emission and in reception is then calculated at point P for the ultrasonic receiving transducer TRj. This signal $r_{jk}(t)$ is obtained by summing all the delayed impulse responses in order to compensate for the travel times $d_{ij}/c$. This signal is expressed as follows:

$$r_{jk}(t) = \sum_{i=1}^{M} h_{ijk}\left(t - \frac{d_{ij}}{c}\right) \qquad (3)$$

The signal $S'_k(t)$ corresponding to the point P and the series k of shots, for all the ultrasonic receiving transducers 3a, is the summation of the beam-forming signals of all the receivers:

$$S'_k(t) = \Sigma_{j=1}^{N} r_{jk}(t) \qquad (4)$$

If P is a material point on the surface 21, then the signal S will be a short pulse of maximum amplitude because all the pulses calculated for all the receivers will have the same delay. Otherwise the signal will be more staggered in time and of lower amplitude.

This method makes it possible, in a first approach, to determine the topography of the surface 21, thus a (generally not very precise) image of the surface 21.

For a same point P of the surface, the successive signals $S'_k(t)$ corresponding to the different measuring steps k make it possible to determine, with great precision, the travel δ of the point P between two successive series of shots k and k+1, during at least one movement determination step.

In all the embodiments of the invention, the steps of movement determination can be carried out as the measuring steps are carried out. Of course, this calculation can also be done on a deferred basis.

If the point P has moved between t and t+dt by a δ distance normal to the surface 21, then the new signal $S'_{k+1}(t)$ will be a time-delayed pulse (counted relative to incident waves shot) with respect to $S'_k(t)$ from dt=2δ cos θ, with the notations already defined above.

The time shift dt gives the travel of the surface 21 at point P:

$$\delta = dt \cdot c / (2 \cos \theta) \tag{5}$$

Back tracking to the normal speed of the surface can easily be performed: V=δ/Δt, where Δt is the time interval between the series of shots k and k+1.

As in method 1, the travel and speed of the surface 21 can be determined in an equivalent way by using the phase shift φ between the signals $S'_k(t)$ and $S'_{k+1}(t)$.

Method 2 is very accurate and can make it possible to measure surface movement with an amplitude well below the wavelength. A parabolic or higher order interpolation can then be used to calculate the time shift to the nearest fraction of the acoustic signals sampling period.

Method 3

In this third method, the network of emitting transducers 2 can be of the multiplied aperture type or have a mixing cavity 4.

The emitted waves reflect on the surface 21 and are collected by the N ultrasonic receiving transducers 3a. The wave path from the surface 21 to the receivers will be considered as direct without any reflection.

This method 3 includes at least one calibration step (a preliminary step which can be repeated at regular intervals for recalibration purposes) during which the impulse responses hij(t) between the ultrasonic emitting transducers TEi and the ultrasonic receiving transducers TRj are determined. After a Fourier transform, these impulse responses are noted Hij (the angular pulsation ω is omitted to simplify the calculations). This preliminary step can possibly be performed by having a pulse emitted successively by each ultrasonic emitting transducer TEi, as in method 2 above.

This preliminary step is followed by several successive measuring steps, indexed by an index k. During each measuring step k, the incident wave is focused successively on the different points P of the surface 21, which points P have been for example determined during the preliminary step.

These successive focusing operations are carried out as follows.

According to the time reversal method and using the principle of reciprocity, by having the emitter i emitting the inverted time impulse response (i.e. in the frequency domain, Hij*, where the exponent * denotes the conjugate complex) the following response should be obtained: Rij=Hij Hij*=|Hij|². The answer Rij is real and corresponds to an impulse centred on the origin of time. According to this observation, it is therefore possible to send a pulse to any one of the receivers j with a certain delay by simply emitting the temporally reversed and delayed impulse response.

In fact, it is possible to emit any wavefront towards all the receivers from a single emitter i. This wavefront being described simply by an arrival delay noted Tj at the receiver j. For this purpose, combining the signals before having them re-emitted by the ultrasonic emitting transducer TEi is sufficient:

$$E_i = \Sigma_{j=1}^{N} H_{ij}^* e^{-j\omega T_j} \tag{6}$$

where Ei is the signal emitted by the ultrasonic emitting transducer TEi, in the frequency domain.

A spherical wavefront arriving at the ultrasonic receiving transducers TRj, resulting from a centre of divergence constituted by a point P on the surface 21 can therefore be synthesized. In other words, the incident ultrasonic wave can be focused at point P on the surface 21.

This wavefront synthesis is further enhanced when all the ultrasonic emitting transducers TEi emit the signals required for the synthesis of the same wavefront. In matrix notation, the signals emitted by all the ultrasonic emitting transducers TEi can be written as follows:

$$E = \begin{bmatrix} E_1 \\ E_2 \\ \vdots \\ E_M \end{bmatrix} = \begin{pmatrix} H_{11}^* & \cdots & H_{1N}^* \\ \vdots & \ddots & \vdots \\ H_{M1}^* & \cdots & H_{MN}^* \end{pmatrix} \begin{bmatrix} e^{-j\omega T_1} \\ e^{-j\omega T_2} \\ \vdots \\ e^{-j\omega T_N} \end{bmatrix} \tag{7}$$

At the ultrasonic receiving transducers TRj, the received signals are:

$$R_j = \Sigma_{i=1}^{M} E_i H_{ij} \tag{8}$$

In a matrix form this can be summarized as follows:

$$R = \begin{bmatrix} R_1 \\ R_2 \\ \vdots \\ R_M \end{bmatrix} = \begin{pmatrix} H_{11} & \cdots & H_{M1} \\ \vdots & \ddots & \vdots \\ H_{1N} & \cdots & H_{MN} \end{pmatrix} \begin{bmatrix} E_1 \\ E_2 \\ \vdots \\ E_M \end{bmatrix} = HE \tag{9}$$

All the signals received by the various ultrasonic receiving transducers TRj can be combined after focusing at point P of the surface 21, by performing beam-forming by compensating for delays in the received signals before the summation thereof:

$$S_k = \Sigma_{j=1}^{N} R_j e^{+j\omega T_j} = [e^{+j\omega T_1}\ e^{+j\omega T_2} \ldots e^{+j\omega T_N}] R = TR \tag{10}$$

The index k refers to the measuring step, i.e. a succession of incident wave shots successively focused on the various points P considered of the surface 21.

In a matrix notation, focusing at point P in emission and beam-forming in reception is reduced to the following single signal:

$$S_k = TR = THE = THH^{T*} T^{T*} \tag{11}$$

The exponent T* indicates that the matrix is transposed conjugated.

The signal $S_k$ mainly represents the information collected at the point P.

When this point moves between the measuring step k and the measuring step k+1, the result is a phase shift φ between $S_k$ and $S_{k+1}$.

This phase shift φ makes it possible to trace back to the travel δ of the surface 21 at the point P using the formula (2) mentioned above, or to the travel speed V as explained in method 1, during at least one movement determination step.

It should be noted that the above calculations of the third method could also be done in the time domain rather than in the frequency domain. Conversely, the calculations of methods 1 and 2 could also possibly be made in the frequency domain.

In the different methods envisaged, according to the applications, the values of δ and V could be values proportional to the above formulas.

Alternative Solution

The beam-forming in reception can possibly be carried out with a mixer, as explained in the following documents:

Nicolas Quieffin, Stefan Catheline, Ros Kiri Ing and Mathias Fink, "Acoustic source localization model using in-skull reverberation and time reversal", Applied Physics Letters vol. 90, 063902 (2007)];

N. Etaix, M. Fink and R. K. Ing, "Acoustic imaging device with one transducer", J. Acoust. Soc. Am. 131 (5), pp. EL395-EL399, 2012;

N. Etaix, J. Dubois, M. Fink and R. K. Ing, "Increasing the modal density in plates for mono-element focusing in air", J. Acoust. Soc. Am., Vol. 134 (2), pp. 1049-1054, 2013.

Figure 6:
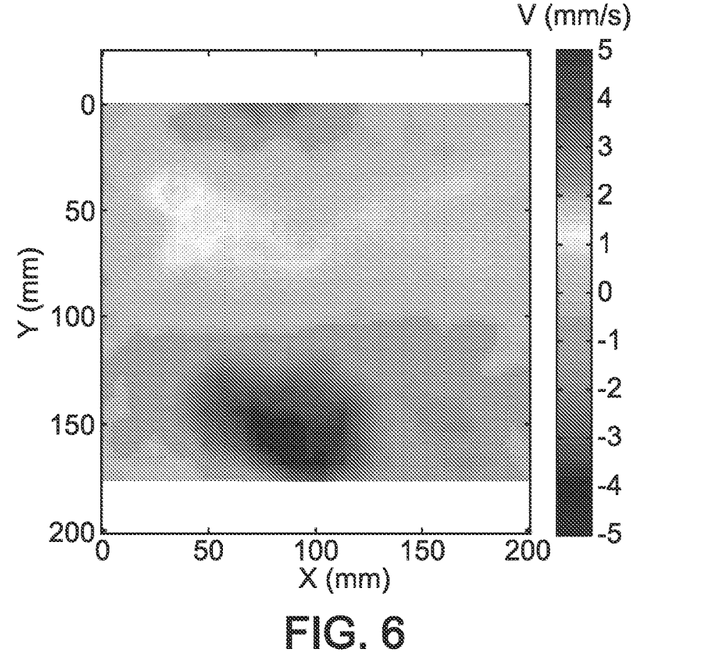
FIG. 6 is an example of mapping of the travel speeds of a surface measured by the device of FIGS. 1 to 5.
Figure 7:
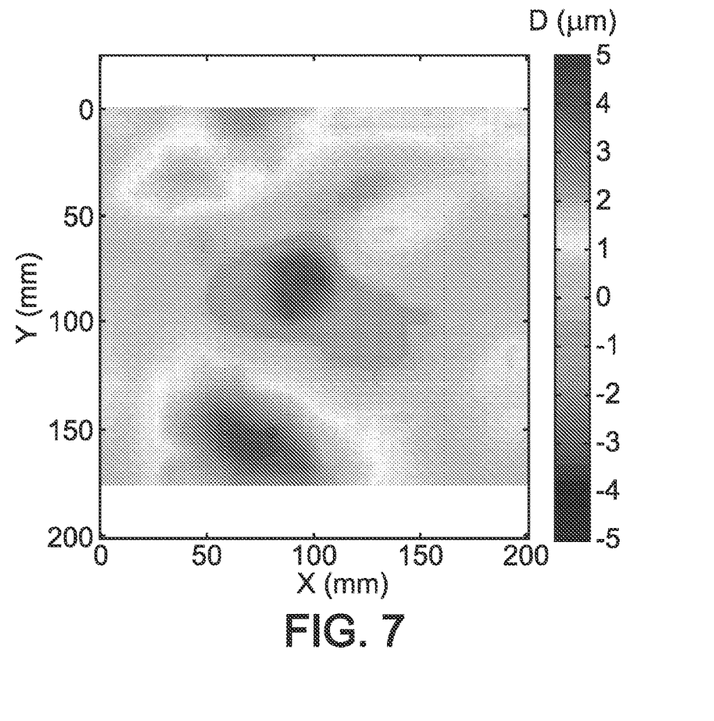
FIG. 7 is an example of mapping of the travels of a surface measured by the device of FIGS. 1 to 5.
Figure 8:
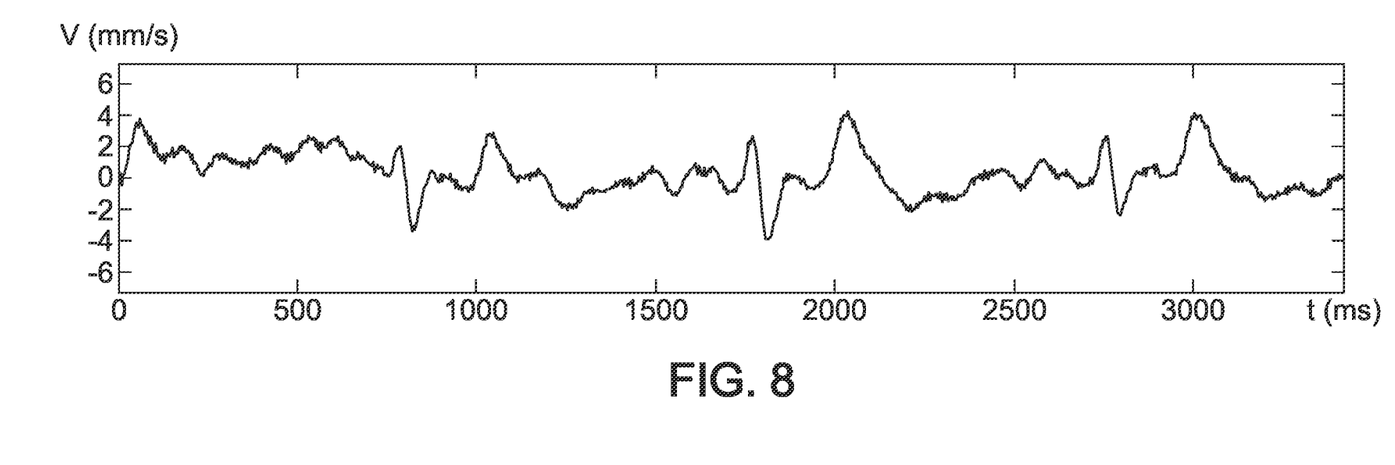
FIG. 8 is an example of a curve of the travel speeds of a point of the surface over time, as measured by the device of FIGS. 1 to 5.
Figure 9:
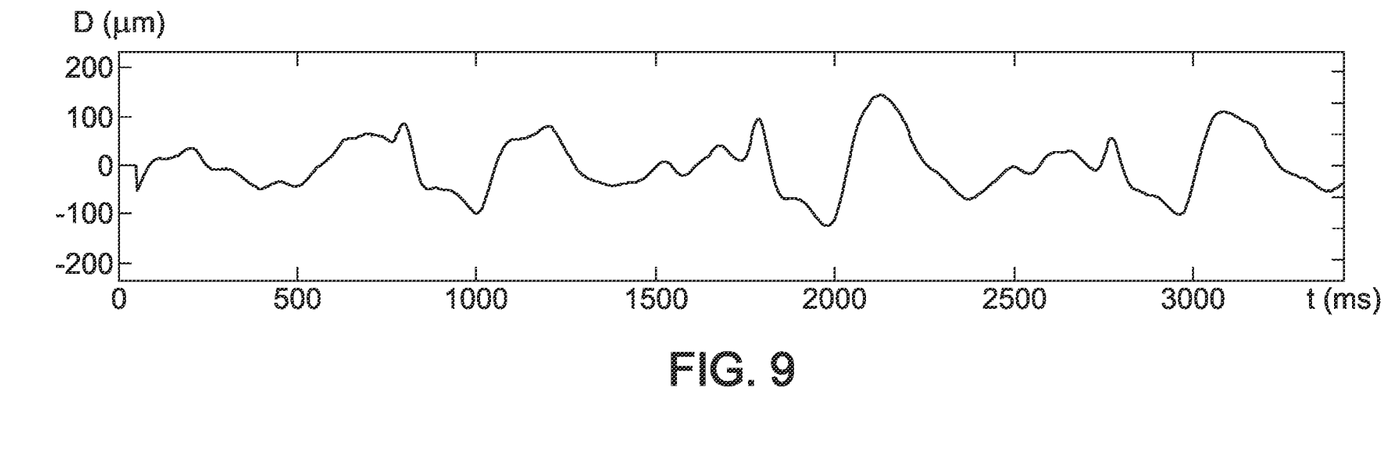
FIG. 9 is an example of a curve of the travels of a point of the surface over time, as measured by the device of FIGS. 1 to 5.

FIGS. 6 and 7 show an example of mapping the travel speeds and travels measured by the method according to the invention on the surface 21 of the lower sternum of the human body, caused to vibrate by heartbeats. FIGS. 8 and 9 show the evolution over time of the travel speeds and travels measured by the method according to the invention on the same solid surface 21.

The invention is therefore particularly useful for the analysis of surface movements of the human body, particularly for the study of respiratory movements or of the cardiovascular system.

The invention is particularly advantageous, particularly in the study of pulmonary ventilation, since it makes it possible to trace back to variations in lung volume and therefore to the flow rates of air inhaled/exhaled without disturbing the subject, unlike procedures involving, for example, a mouthpiece or a face mask.

The invention also makes it possible to automatically monitor a patient's breathing, for example in intensive care, waking up from anaesthesia, in the waiting room in the emergency room, or for infants at risk, etc.

Outside the medical field, the invention can also make it possible, for example, to early detect a person falling asleep, to detect a situation of stress in a person, etc.

Finally, outside the medical field, the invention can also detect objects fixed on the skin and hidden by a tissue. By exciting the subject and more particularly the observed area, the surface movement of the skin will be disrupted by the hidden object(s) and will be observable by the device claimed in this document.

The invention claimed is:

1. A method for detecting movements of a surface (21) reflecting ultrasonic waves, comprising several successive measuring steps during each of which at least one incident ultrasonic wave is emitted into the air towards the surface (21) using an ultrasonic wave emitting device (2) and reflected signals representative of at least one ultrasonic wave reflected in the air by said surface (21) from said at least one incident ultrasonic wave are detected, characterized in that, during each measuring step:
   the movements of a plurality of measuring points (P) belonging at least to said surface are measured by illuminating each measuring point (P) with said at least one incident ultrasonic wave at a multiplicity of angles of incidence,
   the reflected signals are detected using a network of receiving transducers (3) comprising a plurality of ultrasonic receiving transducers (3*a*) and a beam-forming signal is determined for each measuring point (P), by at least beam-forming in reception from said reflected signals,
   and in that it further comprises at least one movement determination step during which said movements of the surface (21) at the considered measuring point (P) are determined by determining at least one delay or phase shift between two beam-forming signals for this measuring point (P).

2. The method according to claim 1, wherein during each measuring step, each measuring point (P) of the surface (21) is illuminated with said at least one incident wave at angles of incidence extending over a range of angles of incidence of at least 20 degrees.

3. The method according to claim 1, wherein, during each measuring step, the movements are measured at substantially any point of the surface (21) over an area greater than 10 $cm^2$.

4. The method according to claim 1, wherein the ultrasonic wave emitting device (2) and the network of receiving transducers (3) are two-dimensional.

5. The method according to claim 4, wherein the network of emitting transducers (2) has an aperture ($OE_Y$, $OE_Z$, $OE'_Y$, $OE'_Z$) at least equal to an aperture ($OR_Y$, $OR_Z$) of the ultrasonic wave receiving device (3) in two substantially perpendicular directions.

6. The method according to claim 5, wherein the aperture ($OE_Y$, $OE_Z$, $OE'_Y$, $OE'_Z$) of the network of emitting transducers (2) is equal to at least three times the aperture ($OR_Y$, $OR_Z$) of the ultrasonic wave receiving device (3), in at least one of the directions.

7. The method according to claim 4, wherein the aperture ($OE_Y$, $OE_Z$, $OE'_Y$, $OE'_Z$) of the ultrasonic wave emitting device (2) is at least equal to 20 cm in each direction.

8. The method according to claim 1, wherein the ultrasonic wave emitting device (2) comprises a network of emitting transducers (2) comprising a plurality of ultrasonic emitting transducers (2*a*).

9. The method according to claim 8, wherein the ultrasonic emitting transducers (2*a*) are divided into several groups and during said measuring step, a same signal is simultaneously emitted by the ultrasonic emitting transducers (2*a*) belonging to a same group.

10. The method according to claim 1, wherein the ultrasonic wave emitting device (2) comprises at least one ultrasonic emitting transducer (2*a*) so arranged as to emit into a mixing cavity (4) adapted to cause multiple reflections of said at least one incident ultrasonic wave before sending it towards the surface (21).

11. The method according to claim 1, wherein the ultrasonic waves have a frequency of less than 100 kHz.

12. The method according to claim 1, wherein the ultrasonic waves are emitted at a rate above 500 shots per second.

13. The method according to claim 1, wherein, during each step of measuring index k, a beam-forming signal $S_k$ in reception is calculated at said point (P), at least at different points (P) of the surface (21),
   and in each movement determination step, the movement of each point (P) of the surface (21) is determined by determining a delay or phase shift between the beam-forming signals $S_k$ in reception at said point (P), for two different k values.

14. The method according to claim 13, wherein during each step of measuring index k, the ultrasonic wave emitting device (2) emits a non focused incident ultrasonic wave towards the surface (21).

15. The method according to claim 13, wherein, during each step of measuring index k, the ultrasonic wave emitting device (2) successively emits focused incident ultrasonic waves towards the different points (P) of the surface (21) and the beam-forming signal $S_k$ in reception at said point (P) is determined from the reflected signals corresponding to the focused incident ultrasonic wave at said point (P).

16. The method according to claim 13, wherein the beam-forming signal $S_k$ in reception is determined by the following formula:

$$S_k(t) = \sum_{j=1}^{N} r_j\left(t - \frac{d_j}{C}\right)$$

where:
- $r_j$ is the signal detected by the ultrasonic receiving transducer (3a) of index j,
- t is time,
- $d_j$ is a distance between the point P and the ultrasonic receiving transducer (3a) of index j,
- c is the speed of the ultrasonic wave in the air.

17. The method according to claim 1, wherein the ultrasonic wave emitting device (2) comprises a network of emitting transducers (2) comprising a plurality of ultrasonic emitting transducers (2a), during each k-index measuring step, respective impulse responses are measured between each ultrasonic emitting transducer (2a) and each ultrasonic receiving transducer (3a), and then at least at different points (P) of the surface (21) a beam-forming signal $S'_k$ in emission and in reception is calculated at said point (P), and during each movement determination step, a movement of each point (P) of the surface (21) is determined by determining a delay or phase shift between the beam-forming signals $S'_k$ in emission and in reception at said point (P), for two different k values.

18. The method according to claim 17, wherein each beam-forming signal in emission and in reception at said point (P) is determined by the following formula:

$$S'_k(t) = \sum_{j=1}^{N} \sum_{i=1}^{M} h_{ijk}\left(t - \frac{d_{ij}}{c}\right),$$

where:
- i is an index between 1 and M referring to an ultrasonic emitting transducer (2a),
- j is an index between 1 and N referring to an ultrasonic receiving transducer (3a),
- $h_{ijk}$ is the impulse response between the ultrasonic emitting transducer (2a) of index i and the ultrasonic receiving transducer (3a) of index j,
- t is time,
- $d_{ij}$ is a distance travelled by an ultrasonic wave from the ultrasonic emitting transducer (2a) of index i to the ultrasonic receiving transducer (3a) of index j by reflecting at the considered point (P) of the surface (21),
- c is the speed of the ultrasonic waves in the air.

19. The method according to claim 1, wherein, during at least some measuring steps, a beam-forming signal is determined for each measuring point (P) of a predetermined observation area and the measuring points (P) belonging to the surface (21) are determined as those which maximize the beam-forming signal.

20. The method according to claim 1, wherein, during the movement determination step, a delay dt between beam-forming signals corresponding to two measuring steps at the same measuring point (P) is determined and:
- a travel δ at the measuring point (P) as being proportional to dt·c
- and/or a speed at the measuring point (P) as being proportional to dt·c/Δt,
- where c is the speed of the ultrasonic waves in the air and Δt is a time interval between said two measuring steps.

21. The method according to claim 1, wherein, during the movement determination step, a phase shift φ is determined between beam-forming signals corresponding to two measuring steps at the same measuring point (P) and:
- a travel φ at the measuring point (P) as being proportional to c·φ/(2·π·f)
- and/or a speed at the measuring point (P) as being proportional to c·φ/(2·π·f)/Δt,
- where c is the speed of the ultrasonic waves in the air, f is the frequency of the ultrasonic waves and Δt is a time interval between said two measuring steps.

22. A device for detecting movements of a surface (21) reflecting ultrasonic waves, comprising an ultrasonic wave emitting device (2), an ultrasonic wave receiving device (3), a control device (5) controlling the ultrasonic wave emitting device (2) and receiving signals detected by the ultrasonic wave receiving device (3), with the control device (5) being adapted to carry out several successive measuring steps during each of which the ultrasonic wave emitting device (2) emits at least one incident ultrasonic wave into the air towards the surface (21) and the ultrasonic wave receiving device (3) receives reflected signals representative of at least one ultrasonic wave reflected in the air by said surface (21) from said at least one incident ultrasonic wave, characterized in that an ultrasonic wave emitting device (2) is adapted to illuminate a plurality of measuring points (P) belonging at least to said surface (21) by said at least one incident ultrasonic wave at a multiplicity of angles of incidence, in that the ultrasonic wave receiving device (3) is a network of receiving transducers (3) comprising a plurality of receiving ultrasonic transducers (3a), in that the control device (5) is adapted to determine, during each measuring step, a beam-forming signal for each measuring point (P), by at least beam-forming in reception from said reflected signals, and in that the control device (5) is adapted to determine said movements of the surface (21) at the considered measuring point (P) by determining at least one delay or phase shift between two beam-forming signals for that measuring point (P).

* * * * *